United States Patent [19]

Ohsaki et al.

[11] Patent Number: 4,942,143
[45] Date of Patent: Jul. 17, 1990

[54] IMIDAZOTHIADIAZINE DERIVATIVES, AND THEIR USE AS MEDICAMENTS

[75] Inventors: Tsutomu Ohsaki, Saitama; Jinsaku Sakakibara, Nagoya; Takeo Kuriki, Saitama, all of Japan

[73] Assignee: Hoechst Japan Limited, Tokyo, Japan

[21] Appl. No.: 178,231

[22] Filed: Apr. 6, 1988

[30] Foreign Application Priority Data

Apr. 8, 1987 [JP] Japan .................................. 62-86130
Aug. 21, 1987 [JP] Japan .................................. 62-209066

[51] Int. Cl.$^5$ ...................... A61K 31/54; C07D 513/04
[52] U.S. Cl. ...................... 514/222.8; 544/10
[58] Field of Search ...................... 514/222.8; 544/10

[56] References Cited

U.S. PATENT DOCUMENTS

3,217,001 11/1965 Santilli et al. .......................... 544/11
3,493,573 2/1970 Joullie et al. .......................... 260/253

FOREIGN PATENT DOCUMENTS

2083470 3/1982 United Kingdom .

OTHER PUBLICATIONS

Ohsaki et al, Chemical Abstracts, vol. 110, entry 8173u.
Edenhofer et al., Chemical Abstracts, vol. 87:23224m (1977).

G. Garcia-Munoz et al., J. Heterocyclic Chem. vol. 13, No. 4 (1976), pp. 793–796.
J. Barluenga et al., J. Chem. Soc. Perkin Trans. I (1983), pp. 2273–2276.

*Primary Examiner*—John M. Ford
*Attorney, Agent, or Firm*—Finnegan, Henderson, Farabow, Garrett and Dunner

[57] ABSTRACT

The present invention relates to 1,3,6,7-Tetrahydro-7-oxoimidazo[4,5-c][1,2,6]-thiadiazine 2-oxide derivatives of the general formula (I):

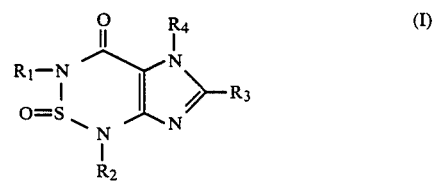

wherein $R_1$, $R_2$ and $R_4$ are the same or different and represent an alkyl group, an aryl group or an aralkyl group, each of which may have one or more substituents; and $R_3$ represents a hydrogen atom, a halogen atom, an alkyl group, an aryl group or an aralkyl group, each of which group may have one or more substituents, and a process for their preparation. The imidazothiadiazine derivatives have hypotensive and vasodilating activities and can therefore be used as medicaments.

5 Claims, No Drawings

IMIDAZOTHIADIAZINE DERIVATIVES, AND THEIR USE AS MEDICAMENTS

DESCRIPTION

The present invention relates to 1,3,6,7-tetrahydro-7-oxoimidazo[4,5-c][1,2,6]thiadiazine 2-oxide derivatives of general formula (I):

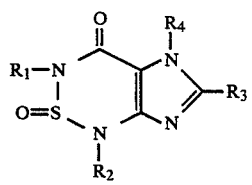

in which $R_1$, $R_2$ and $R_4$ are the same or different and represent an alkyl group, an aryl group or an aralkyl group, each of which may have one or more substituents; and $R_3$ represents a hydrogen atom, a halogen atom, an alkyl group, an aryl group or an aralkyl group, each of which groups may have one or more substituents, and a process for preparing the same. The imidazothiadiazine derivatives are useful as hypotensive and vasodilating agents.

As thiadiazine compounds, there are known monocyclic 1,2,6-thiadiazine S-oxide derivatives (J. Barluenga, M. Tomás, J. F. López-Ortiz and V. Gotor: J. Chem. Soc. Perkin Trans I: 1983, 2273–2276 (1983)). However, no imidazothiadiazine compound having a condensed imidazole ring has been known.

It has not been found, that thiadiazine compounds of the formula I having a condensed imidazole ring exhibit unique pharmacological properties in view of their structural similarity to xanthine compounds.

The present invention relates also to a process for preparing the 1,3,6,7-tetrahydro-7-oxoimidazo[4,5-c][1,2,6]thiadiazine 2-oxide derivatives of the general formula (I), which comprises reacting an imidazole derivative of general formula (III):

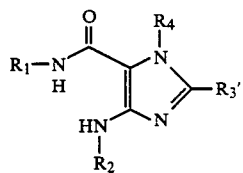

wherein $R_1$, $R_2$ and $R_4$ are as defined above; and $R_3'$ is a hydrogen atom, an alkyl group, an aryl group or an aralkyl group, each of which group may have one or more substituents, with a thionyl halide and, if required, reacting the resulting compound with a halogenating agent.

The compounds according to the present invention are organic three-coordinate sulfur compounds and have the sulfur atom as an asymmetric center. The compounds accordingly exist as optical isomers or racemates. It is thus noted that the imidazothiadiazine derivatives according to the present invention should be construed as encompassing all of their isomers including their racemates and optical isomers. The imidazothiadiazine derivatives as represented by the general formula (I) are novel compounds having an imidazo[4,5-c][1,2,6]thiadiazine skeleton and having potent activities for relaxing blood-vessels, thus being useful as hypotensive drugs and vasodilators.

In the imidazothiadiazine derivatives as represented by the general formula (I), the term "alkyl group" referred to herein is used to mean a straight or branched chain, monovalent saturated hydrocarbon residue having 1 to 10, preferred 1 to 6, particularly preferred 1 to 4 carbon atoms including, for example, methyl, ethyl, propyl, isopropyl, butyl, isobutyl, sec-butyl, tert-butyl, pentyl, isopentyl, tert-pentyl, neopentyl, hexyl, isohexyl, 1-methylpentyl, 2-methylpentyl, 3-methylpentyl, heptyl, octyl, nonyl or decyl. The alkyl group may have one or more substituents including, for example, a halogen atom, an amino group, a mono- or di-$C_1$-$C_6$-alkylamino group, an oxo group, a hydroxyl group, an $C_1$-$C_6$-alkoxy group, a phenoxy group having one or more substituents on its benzene ring, or a heterocyclic group. The alkyl group having a halogen atom as substituent may include, for example, 3-chloropropyl, 4-chlorobutyl, 4-bromobutyl, 6-chlorohexyl or 6-bromohexyl. The alkyl group substituted by di-$C_1$-$C_6$-alkylamino group may include, for example, 4-dimethylaminobutyl or 6-dimethylaminohexyl group. The alkyl group substituted by an oxo group may include, for example, 5-oxohexyl, 6-oxoheptyl, 7-oxooctyl, 8-oxononyl or the 9-oxodecyl group. The alkyl group having an $C_1$-$C_6$-alkoxy group may include, for example, 4-methoxybutyl, 5-methoxypentyl, 5-methoxyhexyl or 6-methoxyhexyl. The alkyl group substituted by a phenoxy group may include, for example, 3-phenoxypropyl, 4-phenoxybutyl, 5-phenoxypentyl or 6-phenoxyhexyl. As the alkyl group substituted by a phenoxy group with the substituent on its benzene ring, there may be exemplified an alkyl group having a phenoxy group substituted by one or more $C_1$-$C_6$-alkyl groups, halogen atoms, hydroxyl groups, $C_1$-$C_4$-alkoxy groups, amino groups, mono- or di-$C_1$-$C_4$-alkylamino groups, oxo-$C_1$-$C_4$-alkyl groups, sulfonamido groups or nitro groups on its benzene ring. Such substituted alkyl group may include, for example, 4-(4-chlorophenoxy)butyl, 5-(4-chlorophenoxy)pentyl, 6-(4-chlorophenoxy)-hexyl, 4-(4-methoxyphenoxy)butyl, 5-(4-methoxyphenoxy)-pentyl or 6-(6-methoxyphenoxy)hexyl. As an alkyl group substituted by a heterocyclic group may be exemplified morpholinopropyl, pyrrolidinopropyl, piperidinobutyl, morpholinobutyl, pyrrolidinobutyl or piperidinobutyl.

The aryl group may specifically include, for example, a phenyl group or a naphthyl group. As specific examples of the substituent on the aryl group may be exemplified $C_1$-$C_4$-alkyl groups, halogen atoms, nitro groups, amino groups, mono- or di-$C_1$-$C_4$-alkylamino groups, hydroxyl groups, $C_1$-$C_4$-alkoxy groups, phenoxy groups, sulfonamido groups or oxo-$C_1$-$C_4$-alkyl groups. The substituted aryl groups may include, for example, 4-chlorophenyl, 3-chlorophenyl, 4-methoxyphenyl, 4-dimethylaminophenyl or 4-hydroxyphenyl.

The aralkyl group may include, for example, a benzyl group or a phenethyl group. As substituents on the aralkyl group, there may be exemplified $C_1$-$C_4$-alkyl groups, halogen atoms, nitro groups, amino groups, mono- or di-$C_1$-$C_4$-alkylamino groups, hydroxyl groups, $C_1$-$C_4$-alkoxy groups, phenoxy groups, sulfonamido groups or oxo-$C_1$-$C_4$-alkyl groups. The substituted aralkyl group may include, for example, 4-chlorobenzyl, 3-chlorobenzyl, 4-methoxybenzyl, 4-dimethylaminobenzyl or 4-hydroxybenzyl.

The term "one or more substituents" as applied to any of the afore-mentioned groups means preferably one to three, most preferably one or two substituents.

The imidazothiadiazine derivatives as represented by the general formula (I) may be prepared by various processes. As representative of such processes will be described the following reaction schemes:

Reaction Scheme 1:

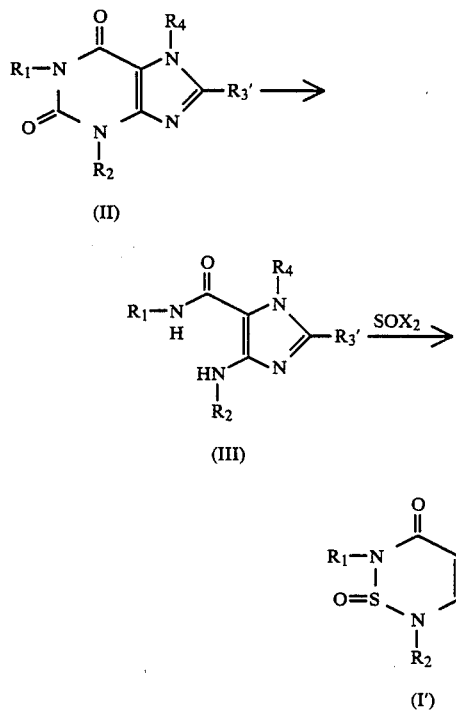

Reaction Scheme 2:

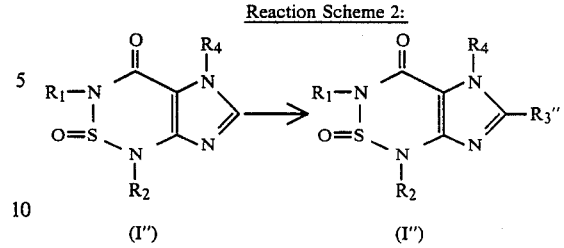

in which $R_3''$ is a halogen atom and $R_1$, $R_2$ and $R_4$ have the same meanings as above.

As shown in Reaction Scheme 2 illustrated hereinabove, the compounds as represented by the general formula (I''') can be prepared by reacting a 1,3,6,7-tetrahydro-7-oxoimidazo[4,5-c]-[1,2,6]thiadiazine 2-oxide derivative as represented by the general formula (I'') with a halogenating agent. As the halogenating agent there can be generally employed thionyl chloride, thionyl bromide, phosphorus oxychloride, phosphorus oxybromide, phosphorus pentachloride, phosphorus pentabromide, sulfuryl chloride, sulfuryl bromide or the like; however, thionyl chloride, thionyl bromide, sulfuryl chloride or sulfuryl bromide are preferably employed. As to thionyl chloride or thionyl bromide, it is preferred to use it in a large excess amount without any other solvent, at ambient or elevated temperatures. As to sulfuryl chloride or sulfuryl bromide, it is preferred to carry out the reaction at ambient temperature in an inert organic solvent such as carbon tetrachloride, chloroform and dichloromethane. The sulfuryl halide may be employed in equimolar or slightly excess amount with respect to the compound as represented by the general formula (I''). Reaction time can conveniently vary depending upon solvent, raw material and reaction temperature.

wherein $R_1$, $R_2$, $R_4$ and $R'_3$ are as defined above and X is a halogen atom.

In the above reactions, the hydrolysis of the 1,3,7-trisubstituted xanthine derivative as represented by the general formula (II) may be preferably carried out in the presence of an inorganic base such as sodium hydroxide and potassium hydroxide, particularly at the concentration of 3–4N, in water or in a mixture of water and an alcohol, under reflux at elevated temperatures. Reaction time is not limited to any particular range of periods and may vary depending upon raw material, solvent and so on.

In the above reactions, the cyclization of the imidazole derivative as represented by the general formula (III) is conducted under dry conditions in a tertiary amine such as pyridine or triethylamine or in an inert solvent such as benzene, toluene, dichlormethane or chloroform with the above-illustrated tertiary amine as a catalyst. The thionyl halide and the catalyst are preferably employed in an equimolar or slightly excess amount with respect to the imidazole derivative as represented by the general formula (III). This reaction is an exothermal one so that it is preferred to conduct the initial stages of the reaction under cooling. Reaction time may be suitably determined in accordance with solvent, reaction and the temperature used.

Among the intermediate compounds used in the above reactions, novel 1,3,7-trisubstituted xanthine derivatives as represented by general formula (VI) below can be prepared by reacting a 3,7-disubstituted xanthine derivative as represented by the general formula (IV) with a phenoxyalkyl halide as represented by general formula (V) in a conventional manner as illustrated by the following reaction scheme:

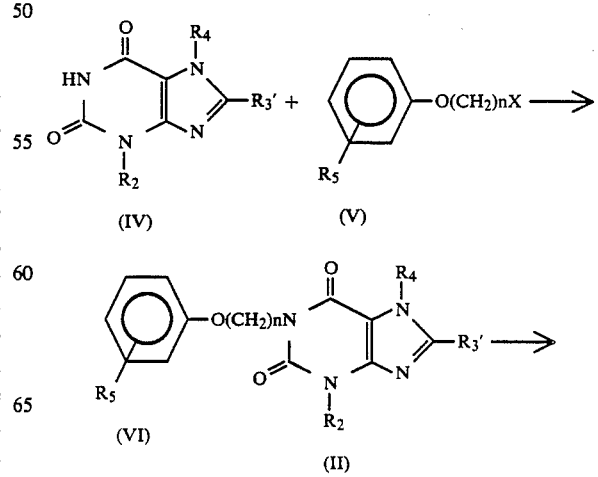

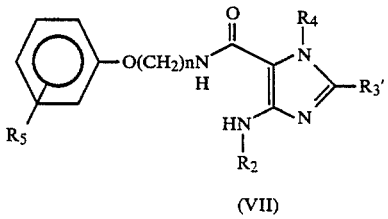

(VII)

wherein $R_2$, $R_3'$ and $R_4$ have the same meanings as above, and $R_5$ is a hydrogen atom, a halogen atom, an alkyl group, a hydroxyl group, an alkoxy group, an amino group, a mono- or di-alkylamino group, an oxoalkyl group, a sulfonamido group or a nitro group, X is chlorine or bromine and n is an integer from 1 to 10.

The 1,3,7-trisubstituted xanthine derivatives as represented by the general formula (VI) can be converted to the compounds as represented by the general formula (I') by subjecting the former to the reaction conditions as illustrated in the Reaction Scheme 1 above.

The intermediate compounds to be produced in each step of the reactions and the imidazothiadiazine derivatives according to the present invention can be isolated or purified in conventional procedures such as extraction, crystallization, recrystallization, chromatography and so on.

The imidazothiadiazine compounds as represented by the general formula (I) and their pharmaceutically acceptable acid addition salts have particularly potent activities of relaxing blood-vessels and thus are useful for controlling high blood pressures originating from various etiological causes. They can be used together with other compounds having hypotensive, vasodilating or diuretic activities, and can be administered intravenously, subcuteneously or orally.

An oral dose for an adult patient with an average weight may be in the range generally from 1 to 500 mg, preferably from 1 to 100 mg. However, an increased dose may be administered to a patient with an advanced disease since no toxicity has been observed up to now. It is further noted that the dose may be decreased according to conditions of illness, and this is particularly effective when it is administered together with a diuretic.

The imidazothiadiazine compounds according to the present invention can be administered orally in various forms such as tablets, capsules, granules, fine granules, powders, aqueous, alcoholic or oleaginous suspensions, solutions or enteric preparations. These formulations can be prepared with conventional additives or auxiliaries such as vehicles, stabilizers or inert diluents in accordance with conventional procedures. Suitable inert vehicles include, for example, gum arabi, gelatin, carboxymethyl cellulose, magnesium carbonate, potassium phosphate, talc, magnesium stearate, anhydrous silicic acid, mannitol, maltose, lactose, glucose or starch, particularly corn starch. As oily vehicles or solvents, there can be used vegetable oil such as sunflower oil or animal oil such as liver oil.

Enteric preparations are prepared by coating tablets, granules or fine granules with one or more enteric bases such as cellulose acetate phthalate, hydroxypropylmethylcellulose acetylsuccinate and maleic anhydride copolymer according to conventional manner.

The imidazothiadiazine compounds according to the present invention can also be administered intravenously or subcuteneously in the form of solutions, suspensions or emulsions. These formulations may be prepared by dissolving, suspending or emulsifying the active components together with dissolving agents, emulsifying agents or other auxiliary agents. As the solvent, water, physiological saline, an alcohol such as ethanol, propanediol and glycerol, or a mixture thereof are preferably used.

The present invention will be described more in detail by the way of examples.

EXAMPLE 1

(a) Hexyltheobromine (7.5 g) was added to 60 ml of 3N sodium hydroxide, and the mixture was refluxed at elevated temperatures for 6 hours. After the reaction mixture was cooled to ambient temperature, it was extracted with chloroform and the extract was dried and concentrated under reduced pressure to give the residue which in turn was subjected to silica gel column chromatography using a chloroform/ethanol (25:2(v/v)) eluent, thereby yielding 2.6 g (38%) of 5-hexylaminocarbonyl-1-methyl-4-methylaminoimidazole as an oil. A portion of this product was then treated with an ethanolic solution of picric acid to give its picrate.

Melting point: 164°–165° C.

IR (KBr) (max) cm$^{-1}$: 3320, 3280, 1625, 1310.

NMR (DMSO-$d_6$) δ: 0.87 (3H, t), 1.1–1.7 (8H, m), 2.84 (3H, s), 3.20 (2H, q), 3.87 (3H, s), 7.59 (1H, t), 8.58 (2H, s), 8.64 (1H, s).

(b) A solution of 2.1 g of the product obtained in (1) above in 40 ml of dry pyridine was cooled in an ice-salt bath and then 1.5 g of thionyl chloride was added dropwise thereto. The solution was then warmed gradually to ambient temperature and stirred for 3 hours. The reaction mixture was concentrated under reduced pressures to give the residue that in turn was subjected to silica gel column chromatography using a chloroform/ethanol (100:1 (v/v)) eluent to yield 1.6 g (64%) of 1-hexyl-1,3,6,7-tetrahydro-3,6-dimethyl-7-oxoimidazo[4,5-c][1,2,6]thiadiazine 2-oxide as an oil.

High Resolution MS ($C_{22}H_{20}N_4O_2S$): Calculated: 284.1306. Found: 284.1285.

IR (Nujol) (max)cm$^{-1}$: 1670, 1130.

NMR (CDCl$_3$) δ: 0.89 (3H, t), 1.1–1.9 (8H, m), 3.63 (1H, q), 3.44 (3H, q), 4.00 (1H, q), 7.44 (1H, s).

EXAMPLE 2

(a) Hexyltheophylline was hydrolyzed and treated in substantially the same manner as described in Example 1 (a) to give 1-hexyl-4-methylamino-5-methylaminocarbonylimidazole (63% yield).

Melting point: 114°–116° C.

IR (KBr) (max)cm$^{-1}$: 3530, 3420, 3300, 1640, 1610.

NMR (CDCl$_3$) δ: 0.87 (3H, t), 1.1–1.5 (6H, m), 1.8–2.0 (2H, m), 2.90 (3H, s), 2.92 (3H, d), 3.52 (1H, bs), 4.23 (2H, t), 7.16 (1H, bs) 7.22 (1H, s).

(b) A solution of 2.4 g of the product obtained in (a) above and 1.3 g of triethylamine in 50 ml of dry pyridine was cooled in an ice-salt bath and then 15 ml of a dry benzene solution containing 1.5 g of thionyl chloride was added dropwise thereto. The temperature of the solution was then warmed gradually to ambient temperature and stirred for 2 hours. The reaction mixture was filtered off and the filtrate was then concentrated under reduced pressures to give the residue that in turn was subjected to silica gel column chromatography using a chloroform/ethanol (40:1 (v/v)) eluent to yield 1.3 g (46%) of 6-hexyl-1,3,6,7-tetrahydro-1,3-dimethyl-7-oxoimidazo[4,5-c][1,2,6]thiadiazine 2-oxide.

Melting point: 62°–63° C.

IR (KBr) (max)cm$^{-1}$: 1675, 1125.

NMR (CDCl$_3$) δ: 0.88 (3H, t), 1.1–1.5 (6H, m), 1.7–2.0 (2H, m), 3.34 (3H, s), 3.45 (3H, s), 4.25 (1H, t), 4.27 (1H, t), 7.45 (1H, s).

Elemental Analysis from C$_{12}$H$_{20}$N$_4$O$_2$S: Calculated: C, 50.68; H, 7.09; N, 19.70. Found: C, 50.87; H, 7.10; N, 19.78.

EXAMPLE 3

(a) Benzyltheobromine was hydrolyzed and treated in substantially the same manner as described in Example 1 (a) to give 5-benzylaminocarbonyl-1-methyl-4-methylaminoimidazole (38% yield).

Melting point: 110°–111° C.

IR (KBr) (max)cm$^{-1}$: 3280, 1600.

NMR (CDCl$_3$) δ: 2.84 (3H, s), 3.74 (1H, bs), 3.86 (3H, s), 4.58 (2H, d), 7.18 (1H, s), 7.32 (5H, s, 1H, bs).

(b) The product obtained in (a) above was cyclized and treated in substantially the same manner as described in Example 1 (b) to give 1-benzyl-1,3,6,7-tetrahydro-3,6-dimethyl-7-oxoimidazo[4,5-c][1,2,6]thiadiazine 2-oxide (93%).

Melting point: 154°–155° C.

IR (KBr) (max)cm$^{-1}$: 1665, 1135.

NMR (CDCl$_3$) δ: 3.44 (3H, s), 3.94 (3H, s), 4.65 (1H, d), 5.38 (1H, d), 7.32 (5H, s), 7.41 (1H, s).

Elemental Analysis from C$_{13}$H$_{14}$N$_4$O$_2$S: Calculated: C, 53.78; H, 4.86; N, 19.30. Found: C, 53.87; H, 4.81; N, 19.27.

EXAMPLE 4

(a) Benzyltheophylline was hydrolyzed and treated in substantially the same manner as described in Example 1 (a) to give 1-benzyl-4-methylamino-5-methylaminocarbonylimidazole (52% yield).

Melting point: 113°–114° C.

IR (KBr) (max)cm$^{-1}$: 3310, 3260, 1620.

NMR (CDCl$_3$) δ: 2.81 (3H, d), 2.91 (3H, s), 4.05 (1H, bs), 5.44 (2H, s), 6.68 (1H, bs), 7.1–7.5 (6H, m).

(b) The product obtained in (a) above was cyclized and treated in substantially the same manner as described in Example 1 (b) to give 6-benzyl-1,3,6,7-tetrahydro-1,3-dimethyl-7-oxoimidazo[4,5-c][1,2,6]thiadiazine 2-oxide (74%).

Melting point: 113°–114° C.

IR (KBr) (max)cm$^{-1}$: 1655, 1135.

NMR (CDCl$_3$) δ: 3.34 (3H, d), 3.46 (3H, s), 5.50 (2H, s), 7.33 (5H, s), 7.43 (1H, s).

Elemental Analysis from C$_{13}$H$_{14}$N$_4$O$_2$S: Calculated: C, 53.78; H, 4.86; N, 19.30. Found: C, 53.50; H, 4.84; N, 19.30.

EXAMPLE 5

(a) 5-Methoxyhexyltheobromine was hydrolyzed and treated in substantially the same manner as described in Example 1 (a) to give 5-(5-methoxyhexyl)aminocarbonyl-1-methyl-4-methylaminoimidazole (29% yield) as an oil.

As picrate:

Melting point: 144°–145° C.

IR (KBr) (max)cm$^{-1}$: 3330, 3280, 1630, 1320.

NMR (DMSO-d$_6$) δ: 1.04 (3H, d), 1.1–1.6 (6H, m), 2.84 (3H, s), 3.19 (3H, s), 3.0–3.3 (3H, m), 3.87 (3H, s), 7.59 (1H, t), 8.58 (2H, s), 8.65 (1H, s).

(b) The product obtained in (a) above was cyclized and treated in substantially the same manner as described in Example 1 (b) to give 1,3,6,7-tetrahydro-1-(5-methoxyhexyl)-3,6-dimethyl-7-oxoimidazo[4,5-c][1,2,6]thiadiazine 2-oxide (84%) as an oil.

High Resolution MS (C$_{13}$H$_{22}$N$_4$O$_2$S): Calculated: 314.1411. Found: 314.1413.

IR (Nujol) (max)cm$^{-1}$: 1670, 1140.

NMR (CDCl$_3$) δ: 1.12 (3H, d), 1.3–2.0 (6H, m), 3.30 (3H, s, 1H, m), 3.45 (3H, s), 3.62 (1H, q), 4.00 (1H, q), 7.41 (1H, s).

EXAMPLE 6

(a) 3-(4-Morpholino)propyltheobromine was hydrolyzed and treated in substantially the same manner as described in Example 1 (a) to give 1-methyl-4-methylamino-5-[3-(4-morpholino)propylaminocarbonyl]imidazole (26% yield) as an oil.

As hydrochloride:

Melting point: 209°–212° C. (decomposed).

IR (KBr) (max)cm$^{-1}$: 3305, 2750–2300, 1660.

NMR (D$_2$O) δ: 2.0–2.3 (2H, m), 2.94 (3H, s), 3.2–4.3 (12H, m), 3.93 (3H, s), 8.32 (1H, s).

(b) The product obtained in (a) above was cyclized and treated in substantially the same manner as described in Example 1 (b) to give 1,3,6,7-tetrahydro-3,6-dimethyl-1-[3-(4-morpholino)propyl]-7-oxoimidazo[4,5-c][1,2,6]thiadiazine 2-oxide (78%).

Melting point: 73°–74° C.

IR (KBr) (max)cm$^{-1}$: 1660, 1130.

NMR (CDCl$_3$) δ: 1.92 (2H, m), 2.30–2.56 (6H, m), 3.44 (3H, s), 3.64–3.84 (4H, m), 3.88–4.24 (2H, m), 3.96 (3H, s), 7.42 (1H, s).

Elemental Analysis from C$_{13}$H$_{21}$N$_5$O$_3$S: Calculated: C, 47.69; H, 6.46; N, 21.39. Found: C, 47.45; H, 6.45; N, 21.39.

EXAMPLE 7

(a) 8-Oxononyltheobromine was hydrolyzed and treated in substantially the same manner as described in Example 1 (a) to give 1-methyl-4-methylamino-5-(8-oxononyl)aminocarbonylimidazole (31% yield) as an oil.

As picrate:

Melting point: 118°–119° C.

IR (KBr) (max)cm$^{-1}$: 3320, 3290, 1710, 1625.

NMR (DMSO-d$_6$) δ: 1.1–1.7 (10H, m), 2.06 (3H, s), 2.40 (2H, t), 2.87 (3H, s), 3.19 (2H, q), 3.87 (3H, s), 7.58 (1H, t), 8.54 (2H, s), 8.64 (1H, s).

(b) The product obtained in (a) above was cyclized and treated in substantially the same manner as described in Example 1 (b) to give 1,3,6,7-tetrahydro-3,6-dimethyl-1-(8-oxononyl)-7-oxoimidazo[4,5-c][1,2,6]thiadiazine 2-oxide (42%).

Melting point: 87°–88° C.

IR (KBr) (max)cm$^{-1}$: 1710, 1655, 1120.

NMR (CDCl$_3$) δ: 1.2–1.8 (10H, m), 2.12 (3H, s), 2.41 (2H, t), 3.45 (3H, s), 3.61 (1H, q), 3.96 (3H, s), 3.97 (1H, q), 7.41 (1H, s).

Elemental Analysis from C$_{15}$H$_{24}$N$_4$O$_3$S: Calculated: C, 52.92; H, 7.11; N, 16.46. Found: C, 52.64; H, 7.08; N, 16.35.

EXAMPLE 8

(a) 4-Phenoxybutyltheobromine was hydrolyzed and treated in substantially the same manner as described in Example 1 (a) to give 1-methyl-4-methylamino-5-(4- phenoxy)butylaminocarbonylimidazole (34% yield) as an oil.

As picrate:
Melting point: 137°-138° C.
IR (KBr) (max)cm$^{-1}$: 3340, 3270, 1630, 1320.
NMR (DMSO-d$_6$) δ: 1.5-1.9 (4H, m), 2.85 (3H, s), 3.28 (2H, q), 3.88 (3H, s), 3.98 (2H, t), 6.8-7.0 (3H, m), 7.1-7.4 (2H, m), 8.65 (1H, s).

(b) The product obtained in (a) above was cyclized and treated in substantially the same manner as described in Example 1 (b) to give 1,3,6,7-tetrahydro-3,6-dimethyl-1-(4-phenoxy)butyl-7-oxoimidazo[4,5-c][1,2,6]thiadiazine 2-oxide (72%).

Melting point: 80°-81° C.
IR (KBr) (max)cm$^{-1}$: 1680, 1250, 1120.
NMR (CDCl$_3$) δ: 1.7-2.1 (4H, m), 3.44 (3H, s), 3.50-3.80 (1H, m), 3.95 (3H, s), 3.98 (2H, t), 4.00-4.30 (1H, m), 6.80-7.03 (3H, m), 7.15-7.38 (2H, m), 7.40 (1H, s).

Elemental Analysis from $C_{16}H_{20}N_4O_3S$: Calculated: C, 55.16; H, 5.79; N, 16.08. Found: C, 54.95; H, 5.73; N, 16.01.

EXAMPLE 9

(a) 3-Methyl-7-propylxanthine (10.4 g) was dissolved in 200 ml of an ethanol/water (3:2 (v/v)) mixed solution containing 2.2 g of sodium hyddroxide and 15.5 g of 4-(4-methoxyphenoxy)butylbromide was added to the solution. The mixture was then refluxed at elevated temperatures for 12 hours. The reaction mixture was concentrated under reduced pressure to give the residual liquid which in turn was alkalized with 1N-sodium hydroxide solution and then extracted with chloroform. The extract was dried and concentrated under reduced pressure to dryness. The residue was then subjected to silica gel column chromatography using a chloroform/ethanol (40:1 (v/v)) eluent to yield 12.5 g (65%) of 1-[4-(4-methoxyphenoxy)butyl]-3-methyl-7-propylxanthine.

Melting point: 61°-62° C.
IR (KBr) (max)cm$^{-1}$: 1700, 1660, 1240.
NMR (DMSO-d$_6$) δ: 0.95 (3H, t), 1.7-2.1 (6H, m), 3.58 (3H, s), 3.75 (3H, s), 3.95 (2H, t), 4.09 (2H, t), 4.25 (2H, t), 6.81 (4H, s), 7.52 (1H, s).

(b) The product obtained in (a) above was hydrolyzed and treated in substantially the same manner as described in Example 1 (a) to give 5-[4-(4-methoxyphenoxy)butylaminocarbonyl]-4-methylamino-1-propylimidazole (26%) as an oil.

As picrate:
Melting point: 82°-83° C.
IR (KBr) (max)cm$^{-1}$: 3410, 3380, 1625, 1225.
NMR (DMSO-d$_6$) δ: 0.81 (3H, t), 1.6-1.9 (6H, m), 2.84 (3H, s), 3.26 (2H, q), 3.69 (3H, s), 3.92 (2H, t), 4.26 (2H, t), 6.84 (4H, s), 7.82 (1H, t), 8.59 (2H, s), 8.73 (1H, s).

(c) The product obtained in (b) above was cyclized and treated in substantially the same manner as described in Example 1 (2) to give 1,3,6,7-tetrahydro-1-[4-(4-methoxyphenoxy)butyl]-3-methyl-6-propyl-7-oxoimidazo[4,5-c][1,2,6]thiadiazine 2-oxide (71%) as an oil.

High Resolution MS ($C_{19}H_{26}N_4O_4S$): Calculated: 406.1674. Found: 406.1666.

IR (Nujol) (max)cm$^{-1}$: 1640, 1220, 1140.
NMR (CDCl$_3$) δ: 0.95 (3H, t), 1.7-2.1 (6H, m), 3.45 (3H, s), 3.64 (1H, q), 3.75 (3H, s), 3.93 (2H, t), 4.04 (1H, q), 4.21 (1H, t), 4.25 (1H, t), 6.81 (4H, s), 7.45 (1H, s).

EXAMPLE 10

(a) 3-Methyl-7-propylxanthine and 6-(4-methoxyphenoxy)hexyl bromide were reacted and treated in substantially the same manner as described in Example 9 (a) to give 1-[6-(4-methoxyphenoxy)hexyl]-3-methyl-7-propylxanthine (47%).

Melting point: 56°-67° C.
IR (KBr) (max)cm$^{-1}$: 1765, 1655, 1240.
NMR (CDCl$_3$) δ: 0.95 (3H, t), 1.3-2.1 (10H, m), 3.58 (3H, s), 3.76 (3H, s), 3.89 (2H, t), 4.02 (2H, t), 4.24 (2H, t), 6.81 (4H, s), 7.52 (1H, s).

(b) The product obtained in (a) above was hydrolyzed and treated in substantially the same manner as described in Example 1 (1) to give 5-[6-(4-methoxyphenoxy)hexylaminocarbonyl]-4-methylamino-1-propylimidazole (48%) as an oil.

As picrate:
Melting point: 99°-100° C.
IR (KBr) (max)cm$^{-1}$: 3440, 3310, 1625, 1335, 1320, 1225.
NMR (DMSO-d$_6$) δ: 0.81 (3H, t), 1.2-1.9 (10H, m), 2.85 (3H, s), 3.23 (2H, q), 3.69 (3H, s), 3.88 (2H, t), 4.27 (2H, t), 6.83 (4H, s), 7.77 (1H, t), 8.59 (2H, s), 8.75 (1H, s).

(c) The product obtained in (b) above was cyclized and treated in substantially the same manner as described in Example 1 (b) to give 1,3,6,7-tetrahydro-1-]6-(4-methoxyphenoxy)hexyl]-3-methyl-6-propyl-7-oxoimidazo[4,5-c][1,2,6]thiadiazine 2-oxide (66%) as an oil.

High Resolution MS ($C_{21}H_{30}N_4O_4S$): Calculated: 434.1986. Found: 434.2007.

IR (KBr) (max)cm$^{-1}$: 1665, 1220, 1135.
NMR (CDCl$_3$) δ: 0.95 (3H, t), 1.3-2.1 (10H, m), 3.45 (3H, s), 3.62 (1H, q), 3.76 (3H, s), 3.89 (2H, t), 4.00 (1H, q), 4.21 (1H, t), 4.25 (1H, t), 6.81 (4H, s), 7.45 (1H, s).

EXAMPLE 11

(a) 7-Hexyl-3-Methylxanthine and 6-(4-methoxyphenoxy)hexyl bromide were reacted and treated in substantially the same manner as described in Example 9 (a) to give 7-hexyl-1-[6-(4-methoxyphenoxy)hexyl]-3-methylxanthine (71%) as an oil.

IR (Nujol) (max)cm$^{-1}$: 1710, 1660, 1230.
NMR (CDCl$_3$) δ: 0.88 (3H, t), 1.1-2.0 (16H, m), 3.58 (3H, s), 3.76(3H, s), 3.89(2H, t), 4.02(2H, t), 4.27(2H, t), 6.81(4H, s), 7.51(1H, s).

(b) The product obtained in (a) above was hydrolyzed and treated in substantially the same manner as described in Example 1(a) to give 1-hexyl-5-[6-(4-methoxyphenoxy)hexylaminocarbonyl]-3-methylimidazole (24%).

Melting point: 35°-36° C.
IR (KBr) (max)cm$^{-1}$: 3420, 3290, 1605, 1230.
NMR(CDCl$_3$) δ: 0.87(3H, t), 1.1-1.9(16H, m), 2.87(3H, s), 3.38(2H,q), 3.76(3H, s), 3.90(2H, t), 4.22(2H, t), 6.81(4H, s), 7.22(1H, s), 7.24(1H, bs).

(c) The product obtained in (b) above was cyclized and treated in substantially the same manner as described in Example 1(b) to give 6-hexyl-1,3,6,7-tetrahydro-1-[6-(4-methoxyphenoxy)hexyl]-3-methyl-7-oxoimidazo[4,5-c][1,2,6]thiadiazine 2-oxide (89%).

Melting point: 56°-57° C.
IR (KBr) (max)cm$^{-1}$: 1680, 1235, 1120.
NMR (CDCl$_3$) δ: 0.88(3H, t), 1.1-2.0(16H, m), 3.45(3H, s), 3.62(1H, q), 3.76(3H, s), 3.89(2H, t), 4.02(1H, q), 4.24(1H, t), 4.28(1H, t), 6.81(4H, s), 7.44(1H, s).

Elemental Analysis from C$_{24}$H$_{36}$N$_4$O$_4$S: Calculated: C, 60.48; H, 7.61; N, 11.75. Found: C, 60.56; H, 7.63; N, 11.88.

EXAMPLE 12

(a) Theobromine and 6-(4-chlorophenoxy)hexyl bromide were reacted and treated in substantially the same manner as described in Example 9(a) to give 6-(4-chlorophenoxy)hexyltheobromine (61%).

Melting point: 97°–98° C.

IR (KBr) (max)cm$^{-1}$: 1720, 1675, 1255.

NMR (CDCl$_3$) δ: 1.3–1.9(8H, m), 3.57(3H, s), 3.91(2H, t), 3.98(3H, s), 4.01(2H, t), 6.79(2H, td), 7.20(2H, td), 7.50 (1H, s).

(b) The product obtained in (a) above was hydrolyzed and treated in substantially the same manner as described in Example 1(a) to give 5-[6-(4-chlorophenoxy)hexylaminocarbonyl]-1-methyl-4-methylaminoimidazole (22%) as an oil.

As picrate:

Melting point: 138°–139° C.

IR (KBr) (max)cm$^{-1}$: 3320, 3270, 1625, 1305, 1240.

NMR (DMSO-d$_5$) δ: 1.2–1.9 (8H, m), 2.85 (3H, s), 3.23 (2H, q), 3.88 (3H, s), 3.95 (2H, t), 6.92 (2H, td), 7.30 (2H, td), 7.61 (1H, t), 8.59 (2H, s), 8.68 (1H, s).

(c) The product obtained in (b) above was cyclized and treated in substantially the same manner as described in Example 1(b) to give 1-[6-(4-chlorophenoxy)hexyl]-1,3,6,7-tetrahydro-3,6-dimethyl-7-oxoimidazo[4,5-c][1,2,6]thiadiazine 2-oxide (79%).

Melting point: 97°–98° C. IR (KBr) (max) cm$^{-1}$: 1660, 1245, 1125.

NMR (CDCl$_3$) δ: 1.3–1.9 (8H, m), 3.44 (3H, s), 3.64 (1H, q), 3.91 (2H, t), 4.00 (1H, q), 6.79 (2H, td), 7.21 (2H, td), 7.41 (1H, s).

Elemental Analysis from C$_{18}$H$_{23}$N$_4$O$_3$SCl: Calculated: C, 52.61; H, 5.64; N, 13.63. Found: C, 52.64; H, 5.67; N, 13.60.

EXAMPLE 13

(a) 3-Methyl-7-propylxanthine and 6-(4-chlorophenoxy)hexyl bromide were reacted and treated in substantially the same manner as described in Example 9(a) to give 1-[6-(4-chlorophenoxy)hexyl]-3-methyl-7-propylxanthine (51%).

Melting point: 50°–51° C.

IR (KBr) (max)cm$^{-1}$: 1700, 1645, 1240.

NMR (CDCl$_3$) δ: 0.95 (3H, t), 1.3–2.1 (10H, m), 3.58 (3H, s), 3.91 (2H, t), 4.01 (2H, t), 4.24 (2H, t), 6.79 (2H, td), 7.21 (2H, td), 7.52 (1H, s).

(b) The product obtained in (a) above was hydrolyzed and treated in substantially the same manner as described in Example 1(a) to give 5-[6-(4-chlorophenoxy)hexylaminocarbonyl]-4-methylamino-1-propylimidazole (38%).

Melting point: 66°–67° C.

IR (KBr) (max)cm$^{-1}$: 3350, 3210, 1640, 1235.

NMR (CDCl$_3$) δ: 0.81 (3H, t), 1.3–2.0 (10H, m), 2.87 (3H, s), 3.38 (2H, q), 3.91 (2H, t), 4.19 (2H, t), 6.79 (2H, td), 7.21 (2H, td), 7.23 (1H, s), 7.32 (1H, bs).

(c) The product obtained in (b) above was cyclized and treated in substantially the same manner as described in Example 1(b) to give 1-[6-(4-chlorophenoxy)hexyl]-1,3,6,7-tetrahydro-3-methyl-6-propyl-7-oxoimidazo[4,5-c][1,2,6]thiadiazine 2-oxide (72%).

Melting point: 62°–63° C.

IR (KBr) (max)cm$^{-1}$: 1670, 1240, 1130.

NMR (CDCl$_3$) δ: 0.95 (3H, t), 1.3–2.1 (10H, m), 3.45 (3H, s), 3.63 (1H, q), 3.91 (2H, t), 4.01 (1H, q), 4.21 (1H, t), 4.25 (1H, t), 6.79 (2H, td), 7.21 (2H, td), 7.45 (1H, s).

Elemental Analysis from C$_{20}$H$_{27}$N$_4$O$_3$SCl: Calculated: C, 54.72; H, 6.20; N, 12.76. Found: C, 54.68; H, 6.15; N, 12.77.

EXAMPLE 14

(a) 7-Hexyl-3-methylxanthine and 6-(4-chlorophenoxy)hexyl bromide were reacted and treated in substantially the same manner as described in Example 9(a) to give 1-[6-(4-chlorophenoxy)hexyl]-7-hexyl-3-methylxanthine (84%) as an oil.

IR (Nujol) (max)cm$^{-1}$: 1705, 1660, 1240.

NMR (CDCl$_3$) δ: 0.88 (3H, t), 1.1–2.0 (16H, m), 3.58 (3H, s), 3.91 (2H, t), 4.02 (2H, t), 4.27 (2H, t), 6.79 (2H, td), 7.20 (2H, td), 7.52 (1H, s).

(b) The product obtained in (a) above was hydrolyzed and treated in substantially the same manner as described in Example 1(a) to give 5-[6-(4-chlorophenoxy)hexylaminocarbonyl]-1-hexyl-4-methylaminoimidazole (29%).

Melting point: 55°–56° C.

IR (KBr) (max)cm$^{-1}$: 3310, 3250, 1615, 1245.

NMR (CDCl$_3$) δ: 0.87 (3H, t), 1.1–1.9 (16H, m), 2.87 (3H, s), 3.53 (2H, q), 3.92 (2H, t), 4.22 (2H, t), 6.79 (2H, td), 7.21 (2H, td), 7.24 (1H, s, 1H, bs).

(c) The product obtained in (b) above was cyclized and treated in substantially the same manner as described in Example 1(b) to give 1-[6-(4-chlorophenoxy)hexyl]-6-hexyl-1,3,6,7-tetrahydro-3-methyl-7-oxoimidazo[4,5-c][1,2,6]thiadiazine 2-oxide (72%).

Melting point: 38°–39° C.

High Resolution MS (C$_{23}$H$_{33}$N$_4$O$_3$SCl): Calculated: 480.1960. Found: 480.1960.

IR (Nujol) (max)cm$^{-1}$: 1660, 1240, 1140.

NMR (CDCl$_3$) δ: 0.88 (3H, t), 1.1–2.0 (16H, m), 3.45 (3H, s), 3.64 (1H, q), 3.91 (2H, t), 4.00 (1H, q), 4.24 (1H, t), 4.28 (1H, t), 6.79 (2H, td), 7.21 (2H, td), 7.44 (1H, s).

EXAMPLE 15

The compound (0.5 g) obtained in Example 3 was added to 15 ml of thionyl chloride, and the mixture was stirred at ca. 50° C. for 24 hours. The reaction mixture was then concentrated under reduced pressure to dryness. The residue was then subjected to silica gel column chromatography using a chloroform/ethanol (25:1 (v/v)) eluent to give 0.16 g (29%) of 1-benzyl-5-chloro-1,3,6,7-tetrahydro-3,6-dimethyl-7-oxoimidazo[4,5-c][1,2,6]thiadiazine 2-oxide.

Melting point: 117°–118° C.

IR (KBr) (max)cm$^{-1}$: 1655, 1140.

NMR (CDCl$_3$) δ: 3.41 (3H, s), 3.92 (3H, s), 4.64 (1H, d), 5.36 (1H, d), 7.32 (5H, s).

Elemental Analysis from C$_{13}$H$_{23}$N$_4$O$_2$SCl: Calculated: C, 48.07; H, 4.03; N, 17.25. Found: C, 47.92; H, 3.93; N, 17.16.

EXAMPLE 16

(a) The compound (1.0 g) obtained in Example 8 was dissolved in 20 ml of dry carbon tetrachloride dissolved, and 5 ml of a carbon tetrachloride solution containing 0.47 g of sulfuryl chloride was added gradually thereto at room temperature while removing moisture. The mixture was then stirred for 2 hours. The reaction mixture was poured into a saturated sodium hydrogen carbonate solution and then extracted with chloroform.

The extract was dried and concentrated under reduced pressure to dryness. The residue was then subjected to silica gel column chromatography using a chloroform eluent to give 0.33 g (30%) of 5-chloro-1,3,6,7-tetrahydro-3,6-dimethyl-1-(4-phenoxy)butyl-7-oxoimidazo[4,5-c][1,2,6]thiadiazine 2-oxide.

Melting point: 69°–71° C.

IR (KBr) (max)cm$^{-1}$: 1660, 1245, 1140.

NMR (CDCl$_3$) δ: 1.7–2.0 (4H, m), 3.41 (3H, s), 3.5–3.8 (1H, m), 3.92 (3H, s), 3.98 (2H, t), 4.0–4.3 (1H, m), 6.80–7.04 (3H, m), 7.16–7.38 (2H, m).

Elemental Analysis from C$_{16}$H$_{19}$N$_4$O$_3$SCl: Calculated: C, 50.19; H, 5.00; N, 14.63. Found: C, 50.10; H, 4.94; N, 14.58.

EXAMPLES 17–21

The following compounds were prepared in substantially the same manner as described in Example 16.

EXAMPLE 17

5-chloro-1,3,6,7-tetrahydro-1-[4-(4-methoxyphenoxy)butyl]-3-methyl-6-propyl-7-oxoimidazo[4,5-c][1,2,6]thiadiazine 2-oxide (20%)

High Resolution MS (C$_{19}$H$_{25}$N$_4$O$_4$SCl): Calculated: 440.1283. Found: 440.1284.

IR (Nujol) (max)cm$^{-1}$: 1660, 1230, 1140.

NMR (CDCl$_3$) δ: 0.97 (3H, t), 1.8–2.1 (6H, m), 3.42 (3H, s), 3.60 (1H, q), 3.75 (3H, s), 3.93 (2H, t), 4.01 (1H, t), 4.26 (1H, t), 4.31 (1H, t), 6.81 (4H, s).

EXAMPLE 18

5-chloro-1,3,6,7-tetrahydro-1-[6-(4-methoxyphenoxy)hexyl]-3-methyl-6-propyl-1,3,6,7-tetrahydro-7-oxoimidazo[4,5-c][1,2,6]thiadiazine 2-oxide (20%)

High Resolution MS (C$_{21}$H$_{29}$N$_4$O$_4$SCl): Calculated: 468.1599. Found: 468.1606.

IR (Nujol) (max)cm$^{-1}$: 1665, 1230, 1140.

NMR (CDCl$_3$) δ: 0.97 (3H, t), 1.3–2.1 (16H, m), 3.42 (3H, s), 3.61 (1H, q), 3.76 (3H, s), 3.89 (2H, t), 4.00 (1H, q), 4.26 (1H, t), 4.31 (1H, t), 6.81 (4H, s).

EXAMPLE 19

5-chloro-6-hexyl-1,3,6,7-tetrahydro-1-[6-(4-methoxyphenoxy)hexyl]-3-methyl-7-oxoimidazo[4,5-c][1,2,6]thiadiazine 2-oxide (25%)

Melting point: 48°–49° C.

IR (KBr) (max)cm$^{-1}$: 1660, 1225, 1140.

NMR (CDCl$_3$) δ: 0.89 (3H, t), 1.1–2.0 (16H, m), 3.42 (3H, s), 3.61 (1H, q), 3.76 (3H, s), 3.89 (2H, t), 3.99 (1H, q), 4.28 (1H, t), 4.33 (1H, t), 6.81 (4H, s).

Elementary Analysis from C$_{24}$H$_{35}$N$_4$O$_4$SCl: Calculated: C, 56.40; H, 6.90; N, 10.96. Found: C, 56.14; H, 6.79; N, 11.13.

EXAMPLE 20

5-chloro-1-[6-(4-chlorophenoxy)hexyl]-1,3,6,7-tetrahydro-3,6-dimethyl-7-oxoimidazo[4,5-c][1,2,6]thiadiazine 2-oxide (20%)

Melting point: 81°–82° C.

IR (KBr) (max)cm$^{-1}$: 1680, 1245, 1140.

NMR (CDCl$_3$) δ: 1.3–1.9 (8H, m), 3.41 (3H, s), 3.63 (1H, q), 3.90 (2H, t), 3.92 (3H, s), 3.95 (1H, q), 6.79 (2H, td), 7.21 (2H, td).

Elemental Analysis from C$_{18}$H$_{22}$N$_4$O$_3$SCl$_2$: Calculated: C, 48.54; H, 4.98; N, 12.58. Found: C, 48.69; H, 4.95; N, 12.43.

EXAMPLE 21

5-chloro-1-[6-(4-chlorophenoxy)hexyl]-1,3,6,7-tetrahydro-3-methyl-6-propyl-7-oxoimidazo[4,5-c][1,2,6]thiadiazine 2-oxide (23%)

Melting point: 83°–84° C.

IR (KBr) (max)cm$^{-1}$: 1665, 1240, 1125.

NMR (CDCl$_3$) δ: 0.97 (3H, t), 1.2–2.1 (10H, m), 3.42 (3H, s), 3.62 (1H, q), 3.91 (2H, t), 3.99 (1H, q), 4.26 (1H, t), 4.30 (1H, t), 6.79 (2H, td), 7.21 (2H, td).

Elemental Analysis from C$_{20}$H$_{26}$N$_4$O$_3$SCl$_2$: Calculated: C, 50.74; H, 5.53; N, 11.83. Found: C, 50.82; H, 5.55; N, 11.68.

EXAMPLE 22

(a) 1,3,7,8-Tetramethylxanthine was hydrolyzed and treated in substantially the same manner as described in Example 1(a) to give 1,2-dimethyl-4-methylamino-5-methylaminocarbonylimidazole (23%) as an oil.

As hydrochloride:

NMR (CDCl$_3$) δ: 2.54 (3H, s), 2.73 (3H, d), 2.88 (3H, s), 7.78 (1H, q).

(b) The product obtained in (a) above was cyclized and treated in substantially the same manner as described in Example 1(b) to give 1,3,6,7-tetrahydro-1,3,5,6-tetramethyl-7-oxoimidazo[4,5-c][1,2,6]thiadiazine 2-oxide (71%).

Melting point: 134°–135° C.

IR (KBr) (max)cm$^{-1}$: 1665, 1120.

NMR (CDCl$_3$) δ: 2.41 (3H, s), 3.32 (3H, s), 3.43 (3H, s), 3.87 (3H, s).

EXAMPLE 23

(a) 1,3,8-Triphenyl-7-propylxanthine was hydrolyzed and treated in substantially the same manner as described in Example 1(a) to give 2-phenyl-4-phenylamino-5-phenylaminocarbonyl-1-propylimidazole (46%).

NMR (CDCl$_3$) δ: 0.83 (3H, t), 1.6–2.1 (2H, m), 4.38–4.56 (2H, m), 6.01 (1H, s), 6.8–7.7 (15H, m), 9.54 (1H, bs).

(b) The product obtained in (a) above was cyclized and treated in substantially the same manner as described in Example 2(b) to give 1,3,6,7-tetrahydro-1,3,5-triphenyl-6-propyl-7-oxoimidazo[4,5-c][1,2,6]thiadiazine 2-oxide (58%).

Melting point: 76°–77° C.

IR (CHCl$_3$) (max)cm$^{-1}$: 1675, 1105.

NMR (CDCl$_3$) δ: 0.87 (3H, t), 1.7–2.1 (2H, m), 4.1–4.6 (2H, m), 7.3–7.7 (15H, m).

EXAMPLE 24

(a) 8-Benzyl-1,3-diphenyl-7-propylxanthine was hydrolyzed and treated in substantially the same manner as described in Example 1(a) to give 2-benzyl-4-phenylamino-5-phenylaminocarbonyl-1-propylimidazole (57%).

NMR (CDCl$_3$) δ: 0.90 (3H, t), 1.4–1.9 (2H, m), 4.14 (2H, s), 4.18–4.37 (2H, m), 5.91 (1H, s), 6.7–7.4 (15H, m), 9.53 (1H, bs).

(b) The product obtained in (a) above was cyclized and treated in substantially the same manner as described in Example 2(b) to give 5-benzyl-1,3,6,7-tetrahydro-1,3-diphenyl-6-propyl-7-oxoimidazo[4,5-c][1,2,6]thiadiazine 2-oxide (77%).

Melting point: 64°–65° C.

IR (CHCl$_3$) (max)cm$^{-1}$: 1675, 1105.

NMR (CDCl$_3$) δ: 0.85 (3H, t), 1.4–1.8 (2H, m), 3.9–4.3 (2H, m), 4.14 (2H, s), 7.1–7.6 (15H, m).

We claim:

1. A compound of the formula I

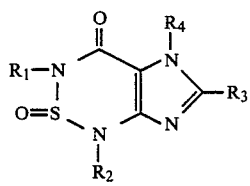

wherein R$_1$, R$_2$ and R$_4$ are each a C$_1$–C$_{10}$-alkyl group unsubstituted or substituted by one or two halogen atoms, oxo groups, amino groups, mono- or di-C$_1$–C$_6$-alkylamino groups, hydroxyl groups, C$_1$–C$_6$-alkoxy groups, phenoxy groups, morpholino groups, pyrrolidino groups, piperidino groups, or phenoxy groups which in turn are unsubstituted or substituted by one or two halogen atoms, C$_1$–C$_4$-alkyl groups, hydroxy groups, C$_1$–C$_4$-alkoxy groups, amino groups, mono- or di-C$_1$–C$_4$-alkylamino groups, oxo-(C$_1$–C$_4$)-alkyl groups, sulfonamido groups or nitro groups, or R$_1$, R$_2$ and R$_4$ represent a phenyl or naphthyl group unsubstituted or substituted by one or two halogen atoms, C$_1$–C$_6$-alkyl groups, nitro groups, amino groups, hydroxyl groups, mono- or di-C$_1$–C$_6$-alkylamino groups, C$_1$–C$_6$-alkoxy groups, phenoxy groups, sulfonamido groups or oxo-C$_1$–C$_6$-alkyl groups; or R$_1$, R$_2$ and R$_4$ represent a benzyl or phenethyl group wherein the benzene ring is unsubstituted or substituted by one or two halogen atoms, nitro groups, hydroxyl groups, amino groups, mono- or di-C$_1$–C$_6$-alkylamino groups, C$_1$–C$_6$-alkoxy groups, phenoxy groups, sulfonamido groups or oxo-C$_1$–C$_6$-alkyl groups; and R$_3$ is a hydrogen atom, a halogen atom, a C$_1$–C$_{10}$-alkyl group which is unsubstituted or substituted by one or two halogen atoms, oxo groups, amino groups, mono- or di-C$_1$–C$_6$-alkylamino groups, hydroxyl groups, C$_1$–C$_6$-alkoxy groups, phenoxy groups, morpholino groups, pyrrolidino groups, piperidino groups or phenoxy groups, which in turn are substituted by one or two halogen atoms, C$_1$–C$_4$-alkyl groups, hydroxy groups, C$_1$–C$_4$-alkoxy groups, amino groups, mono- or di-C$_1$–C$_4$-alkylamino groups, oxo-C$_1$–C$_4$-alkyl groups, sulfonamido groups or nitro groups; or R$_3$ is a phenyl or naphthyl group which is unsubstituted or substituted by one or two halogen atoms, C$_1$–C$_6$-alkyl groups, nitro groups, amino groups, hydroxyl groups, mono- or di-C$_1$–C$_6$-alkylamino groups, C$_1$–C$_6$-alkoxy groups, phenoxy groups, sulfonamido groups or oxo-C$_1$–C$_6$-alkyl groups; or R$_3$ is a benzyl or phenethyl group wherein the benzene ring is unsubstituted or substituted by one or two halogen atoms, nitro groups, hydroxyl groups, amino groups, mono- or di-C$_1$–C$_6$-alkylamino groups, C$_1$–C$_6$-alkoxy groups, phenoxy groups, sulfonamido groups or oxo-C$_1$–C$_6$-alkyl groups.

2. A compound as defined in claim 1, wherein R$_1$ is an unsubstituted C$_1$–C$_{10}$-alkyl group, a phenyl group, a benzyl group or a C$_1$–C$_{10}$-alkyl group which is substituted by an oxo group, a C$_1$–C$_4$-alkoxy group, a phenoxy group, a morpholino group or a phenoxy group which in turn is substituted by a halogen atom or a C$_1$–C$_4$-alkoxy group; R$_2$ is a C$_1$–C$_6$-alkyl group or a phenyl group; R$_3$ is a hydrogen atom, a halogen atom, a C$_1$–C$_6$-alkyl group, a phenyl group or a benzyl group; and R$_4$ is a C$_1$–C$_{10}$-alkyl group or a benzyl group.

3. A compound as defined in claim 1, wherein R$_1$ is an unsubstituted C$_1$–C$_{10}$-alkyl group, a phenyl or benzyl group or a C$_1$–C$_{10}$-alkyl group, which is substituted by an oxo group, methoxy, morpholino, phenoxy or phenoxy substituted by chlorine or methoxy; R$_2$ is methyl or phenyl, R$_3$ is hydrogen, methyl, phenyl, benzyl or chlorine and R$_4$ is C$_1$–C$_6$-alkyl or benzyl.

4. A pharmaceutical composition which comprises as the active ingredient an effective amount of a compound as defined in claim 1 or a pharmacologically acceptable acid addition salt thereof and a pharmaceutically customary carrier and/or auxiliary.

5. A method for the treatment of a patient in need of hypotensive and vasodilating activity which comprises administering to said patient an amount effective for said treatment of a compound of the formula 1 as defined in claim 1 or a pharmacologically acceptable acid addition salt thereof.

* * * * *